United States Patent [19]
Mahr et al.

[11] Patent Number: 5,501,954
[45] Date of Patent: Mar. 26, 1996

[54] METHOD OF DETECTING CELLULAR MATERIAL

[75] Inventors: Anna M. Mahr, Natick; Ann E. Bowe, Needham; Alyson L. Ruff-Roberts, Holliston; Katherine W. Klinger, Sudbury, all of Mass.

[73] Assignee: Genzyme Corporation, Cambridge, Mass.

[21] Appl. No.: 259,224

[22] Filed: Jun. 13, 1994

[51] Int. Cl.$^6$ .............................. C12Q 1/68; C12Q 1/70; G01N 33/53; C07H 21/04
[52] U.S. Cl. .................................. 435/6; 435/5; 435/7.1; 435/91.2; 536/24.3
[58] Field of Search .................................. 435/6, 5, 91.2, 435/91.1, 7.1; 536/24.3–24.33

[56] References Cited

U.S. PATENT DOCUMENTS

| | | | |
|---|---|---|---|
| 4,499,183 | 2/1985 | Sujansky et al. | 435/6 |
| 5,187,083 | 2/1993 | Mullis | 435/91 |
| 5,326,691 | 7/1994 | Hozier | 435/6 |
| 5,366,867 | 11/1994 | Kawakami et al. | 435/8 |

OTHER PUBLICATIONS

Levedakou et al, Biotechniques vol. 7(5) 442–447, 1989.
Melchers et al. J. of Clinical Microbiology 27(1)106–110, 1989.
Klinger, K. et al. (1992) "Rapid Detection of Chromosome Aneuploidies in Uncultured Amniocytes by Using Fluorescense In Situ Hybridization (FISH)" *Am. J. Hum. Genet*, 51:55–65.
Svoboda, K. K. H. (1991) "Intracellular localization of types I and II collagen mRNA and endoplasmic reticulum in embryotic corneal epithelia" *Journal of Cell Science*, 100:23–33.
Tkachuk, D. C. et al. (1991) "Clinical Applications of Fluorescence in situ Hybridization" *GATA*, 8(2):67–74.
Johnson, C. V. et al. (1991) "Fluorescent Detection of Nuclear RNA and DNA: Implication for Genome Organization" *Methods Cell Bio*, vol. 35, Chap 3, pp. 73–99.
Lawrence, J. B. et al. (1990) "Interphase and Metaphase Resolution of Different Distances Within the Human Dystophin Gene" *SCIENCE*, 249:928–932.

Lichter, P. et al. (1988) "Rapid detection of human chromosome 21 aberrations by in situ hybridization" *Proc. Natl. Acad. Sci.*, 85:9664–9668.
Cremer, T. et al. (1988) "Rapid Interphase and Metaphase Assessment of Specific Chromosomal Changes in Neuroectodermal Tumor Cells by in Situ Hybridization with Chemically Modified DNA Probes" *Experimental Cell Research*, 176:199–200.
Lawrence, J. B. et al. (1988) "Sensitive, High Resolution Chromatin and Chromosome Mapping In Situ: Presence and Orientation of Two Closely Integrated Copies of EBV in a Lymphoma Line" *Cell*, 52:51–61.
Landegent, J. E. et al. (1987) "Use of whole cosmid cloned genomic sequences for chromosomal localization by non--radioactive in situ hybridization" *Hum Genet*, 77:366–370.
Bianchi, D. W. et al. (1987) "Direct Hybridization to DNA From Small Numbers of Flow–Sorted Nucleated Newborn Cells" *Cytometry*, 8:197–202.
Pinkel, D. et al. (1986) "Cytogenetic analysis using quantitative, high–sensitivity, fluorescence hybridization" *Proc. Natl. Acad. Sci*, 83:2934–2938.
Brigati, D. J. et al. (1983) "Detection of Viral Genomes in Cultrued Cells and Paraffin–Embedded Tissue Sections Using Biotin–Labeled Hybridization Probes" *VIROLOGY*, 126:32–50.

*Primary Examiner*—W. Gary Jones
*Assistant Examiner*—Dianne Rees
*Attorney, Agent, or Firm*—F. Brad Salcedo

[57] ABSTRACT

The method of the present invention relates to a rapid procedure for detecting DNA in a cell, while preserving the morphology of the nucleus for analysis. The method comprises depositing a cell onto a polymeric membrane filter wherein the DNA contained in the cell is retained on the polymeric membrane filter and is available for binding with a fluorescently labeled nucleic acid probe, incubating the polymeric membrane filter with the labeled nulceic acid probe, and detecting the labeled nulceic acid probe wherein detection of the nulceic acid probe is indicative of the presence of the DNA. There are no separate permeabilization steps needed to permit the probes to enter the cell and hybridize to the DNA. The method is simple and quick and is applicable to the sample volumes found in clinical laboratories.

24 Claims, No Drawings

METHOD OF DETECTING CELLULAR MATERIAL

BACKGROUND OF THE INVENTION

Techniques such as molecular cloning, Southern blotting, Northern blotting and in situ hybridization exploit the specificity and sensitivity of nucleic acid hybridization. These procedures routinely employ polynucleotide probes of high specific radioactivity coupled with autoradiographic detection methods.

Fluorescence in situ hybridization (FISH) is an important and powerful diagnostic tool that helps bridge the resolution gap between chromosome analysis and molecular techniques. The ability to label DNA probe sets and to hybridize them to cytogenetic preparations demonstrates that this technology can be used to detect minute chromosomal abnormalities. The high resolution of this technique allows direct visualization of single copy sequences. Because each chromosome occupies a distinct domain or discrete focal territory in the interphase nucleus (Lichter, P., et al., *PNAS USA.* 85:9664–9668, 1988; Manuelidis, L. *Hum. Genet.* 71:288–293, 1985; Cremer, T. et al., *Exp. Cell Res.* 176:199–220, 1988), a discrete FISH signal is obtained in most nuclei for each specific chromosome present. Therefore, an interphase nucleus with three copies of chromosome 13 will show three chromosome 13 FISH signals while a normal disomic nucleus will have 2 signals. Appropriate probe sets based on cosmid contigs that are chromosome specific can be used to enumerate chromosomes in prenatal diagnostics. Trisomic karyotypes have been diagnosed by FISH procedures (Lichter, P., et al., *PNAS USA.* 85:9664–9668, 1988; Klinger, K., et al., *Am. J. Hum. Genet.* 51:55–65, 1992). It has been shown that variations in sample preparation for FISH can have major effects on hybridizability and signal quality (Jordan, C. A. 1990. In situ hybridization in cells and tissue sections: a study of myelin gene expression during CNS myelination and remyelination. In: Cheselet M-F (ed) In situ hybridization histochemistry. CRC Press, Boca Raton, pp 39–70; Lichter, J. P., Jaunch, A., Cremer, T., and Ward, D.C. 1990. Detection of Down syndrome by in situ hybridization with chromosome 21 specific DNA probes. In: Patterson, D. (ed) Molecular genetics of chromosome 21 and Down syndrome. Wiley-Liss, New York, pp69–78.; McNeil, et al., *Genet. Anal. Tech. Appl.* 8:41–58, 1991). Optimal FISH parameters are also dependent upon the cell type.

FISH is frequently used in conjunction with chromosome analysis. Most chromosome spreads analyzed in clinical laboratories are derived from abundant sources of artificially induced or naturally dividing cell types (e.g., lymphocytes, amniocytes, bone marrow). In situations where the target cell is not abundant or if it is quiescent or infrequently dividing (e.g., rare cancer cells in Minimal Residual Disease or fetal cells in maternal cell circulation), more cells are accessible to analysis using interphase FISH than analysis based on chromosomes.

Clearly, a need exists for a method of sample capture and analysis that minimizes cell loss (e.g., by reducing the number of cell concentration steps or centrifugation which may be harmful to the cell) and maximizes the access to potentially informative target material. It is apparent that different cell types require different processing steps for optimal FISH results. In addition, a need exists for a process that enables simple, quick, and simultaneous processing of multiple samples.

SUMMARY OF THE INVENTION

The method of the present invention relates to a rapid procedure for detecting DNA in a cell, while preserving the morphology of the nucleus for analysis. The method comprises depositing a cell onto a polymeric membrane filter wherein the DNA contained in the cell is retained on the polymeric membrane filter and is available for binding with a fluorescently labeled nucleic acid probe, incubating the polymeric membrane filter with the labeled nulceic acid probe, and detecting the labeled nulceic acid probe wherein detection of the nulceic acid probe is indicative of the presence of the DNA. There are no separate permeabilization steps needed to permit the probes to enter the cell and hybridize to the DNA. The method is simple and quick and is applicable to the sample volumes found in clinical laboratories.

The method of the present invention allows for analysis with single copy sequence probes of cells, sorted onto, filtered onto, grown on or settled onto polymeric membrane filters. In addition, the method allows for the hybridization of probes containing single copy or repetitive DNA sequences to metaphase chromosomes as well as to interphase nuclei on membrane filters.

DETAILED DESCRIPTION OF THE INVENTION

The method of the present invention is based on the discovery that cells can be rapidly isolated, with the morphology of the nuclei substantially intact, for microscopic inspection and identification of the cell's DNA (i.e., target DNA, the DNA being analyzed). The use of polymeric membrane filters has many advantages over glass slides, such as allowing the recovery of samples directly onto the membrane filter from a Fluorescence Activated Cell Sorter (FACS) while allowing for the simple removal of excess liquid along with the removal of fluorescent background due to the fluorescence-conjugated monoclonal on the cell surface. Filtration of cells onto membrane filters also reduces the need for centrifugation to concentrate cells. In addition, polymeric membrane filters reduce the number of steps, when running single or multiple samples, required for analysis such as the need for various cell concentration steps (e.g., centrifugation) with the resultant loss of cells.

The method of the present invention is suitable for detecting the DNA of any cell. These include eukaryotic and prokaryotic cells. In a preferred embodiment, the method of the present invention is used to detect the DNA of mammalian cells in a single cell suspension such as red cells, trophoblasts, leukocytes, amniocytes, tumor cells and blastomeres of humans and other mammals. Generally, cells are deposited onto membranes by filtration. Cells can also be settled or grown onto membranes. The exact manner of cell deposition depends on the cell type and upon any previous treatment the cells have undergone.

The term "cellular material" refers to the components of a cell contained anywhere within a cell such as nucleic acids and proteins. Cellular nucleic acids include DNA and RNA. Cellular proteins include those contained in the nuclear matrix and cytoplasm, as well as nucleic acid associated proteins such as histones. The term "nuclear material" refers to material contained anywhere in the nucleus of a cell, including nucleic acids and nuclear proteins.

The term "cell suspension" refers to any liquid containing cells. This includes cells that are normally in a single cell state i.e., are not normally adherent to other cells or part of a structure, tissue, organ. Such cells may be derived from blood or urine. "Cell suspension" also refers to disaggregated cells that originated from parts of structures, tissues or organs and are now suspended in liquid. "Cell suspensions" may contain either homogeneous or heterogeneous cell types that may or may not have originated from the same structure, tissue, organ or organism.

The term "filtering" refers to the application of a liquid sample, containing cells, to a polymeric membrane filter. Filtering is the process of removing cells and/or parts of cells from excess fluid in a liquid sample by passing the sample through a microporous membrane filter. This process removes particles from solution by the use of pressure and retention on the filter. Filtration is the process of physically removing suspended matter from a liquid by forcing the liquid through a porous mechanical barrier or membrane filter. This facilitates the extraction and analysis of the material separated from the fluid.

The term "cell deposition or application" includes filtering and other methods of applying single cells or single cell suspensions onto polymeric membrane filters. These other methods include putting a drop containing a single cell or single cell suspension onto a polymeric membrane filter and allowing it to dry. Another method includes settling (Klinger, K. et al, *Am. J. Hum. Genet.* 51:55–65, 1992).

The term "polymeric membrane" or "polymeric membrane filter" is intended to include organic membrane filters including those made of polycarbonate, polyvinylidene fluoride (PVDF), polysulfone, nylon, cellulosic esters, nitrocellulose, polypropylene and Teflon (PTFE), which have the characteristics of retaining DNA in suitable condition for hybridization, detection and analysis, while remaining intact through the in situ hybridization process.

The term "labeled ligand" is intended to encompass antibodies and nucleic acids (or nucleic acid probes) labeled directly or indirectly with fluorescent dyes such as fluorescein isothiocyanate (FITC), Cy3™, CyR0™, Cy5™ (Biological Detection Systems, Inc., Pittsburgh, Pa.), Cascade Blue™ and Lucifer Yellow (Molecular Probes, Eugene, Oreg.). Labeled nucleic acid probes of the present invention may be labeled directly or indirectly with fluorescent dyes.

The term "binding" is intended to encompass the actions of which antibodies bind their targets and nucleic acids bind their targets, such as through hybridization. In a preferred embodiment, the ligands of the present invention are labeled with biotin (bio) and are detected with fluorescently tagged avidin or streptavidin or are digoxigenin (dig) labeled probes, detected with fluorescently tagged anti-digoxigenin. Alternatively, the DNA ligands can be directly labeled with fluorescent tags. These can be accomplished by standard procedures known by those of skill in the art.

The term "detection" is intended to encompass any method of detection where analysis or detection of the labeled-ligand bound cellular material (i.e., target DNA, etc.) is made possible with the aid of a device. Such devices include microscopes, FACS devices and fluorimeter.

Any method for labeling ligands known by those of skill in the art are suitable for purposes of the method of the present invention. Digoxigenin-11-dUTP (Boehringer Mannheim, Indianapolis, Ind.) or biotin-16-dUTP (Boehringer Mannheim, Indianapolis, Ind.) can be incorporated into DNA probes by nick translation (Rigby, et al., *J. Mol. Biol.*, 113: 23, 1977) or random priming (Feinberg and Vogelstein, *Anal. Biochem.*, 132:6–13,1983). Detection of compounds containing biotin can be accomplished by incubating with avidin conjugated to the fluorophore of choice. Detection of dioxigenin-labeled nucleotides can be done with an anti-digoxigenin antibody conjugated to FITC, Texas Red, rhodamine or any other fluorophore. Monoclonal antibodies are often detected with secondary antibodies conjugated to the fluorophore of choice (FITC, Cy3™, CyR0™, rhodamine, Cascade Blue™ or Texas Red). Detection of DNA can be accomplished by staining with DNA binding dyes such as DAPI, acridine orange, propidium iodide, and Hoechst dyes. Other DNA binding dyes include those from Molecular Probes: YOYO™, YO-PRO™, TOTO™, TO-PRO™, and SYBR™.

As stated above, the method of the present invention comprises filtering the cells onto a polymeric membrane filter which is porous. The membrane filters of the present invention may be placed onto an apparatus such as a scintered glass filter holder to maintain the rigidity of the membrane during filtering. FISH results can vary, depending on the exact filter holder or device employed. It should be noted that a support made of CellMicroSieves™ (5 μm; Biodesign Inc. of New York, Carmel, N.Y.) inserted between the membrane filter and a vacuum device has been found to generally enhance the signal of the labeled ligand detected, and the morphology and distribution of the cellular material retained on the membrane filter. Additionally, a flatter filter can be obtained facilitating microscopic analysis. It is not absolutely necessary, and whether or not to include it in the protocol needs to be determined empirically.

Any polymeric membrane filter which allows for the filtering of a liquid sample, containing cells or nuclei, and which retains the cellular material of the cell or the nuclei while allowing passage of the liquid portion of the sample and which allows for the subsequent microscopic detection of the retained cellular material without sufficient autofluorescence to interfere with analysis of the desired signal, is suitable in the method of the present invention. In addition, the membrane must retain the cellular material through a series of treatments and washes and remain intact (i.e., not break apart). For example, some nitrocellulose membranes are too brittle for purposes of the present invention. Furthermore, the nuclei that are retained must be in a morphological state suitable for microscopic analysis. The membrane filter must also maintain its physical integrity throughout the procedure and remain relatively flat, i.e., not curl up and not dissolve in the reagents employed. Such polymeric membrane filters in descending order of acceptability, include those made of polycarbonate, polyvinylidene fluoride (PVDF), polysulfone, mixed esters of cellulose and nitrocellulose. Some nylon membranes that were tried were unsuitable due to their autofluorescence. It should be noted that it has been found that membrane filters with a pore size of 5 μm or greater are not suitable for certain cells types because of their size, resulting in significant loss of cells. Membranes with pore sizes less than 0.1 μm tend to yield fragmented FISH signals with unfixed cells. Preparation of numerous samples is simplified and multiple membrane filters can be hybridized and washed simultaneously. These latter advantages are crucial for procedures in a clinical laboratory.

Various fixation procedures may be used in the method of the present invention. It should be noted that it has been discovered that certain fixation protocols appear to affect the quality of the signal analyzed or the nuclear morphology. Many fixatives have a detrimental effect on signal quality. Fixatives that have been found to have a beneficial effect include Streck's Tissue Fixative (S.T.F.™; Streck Laboratories, Inc., Omaha, Nebr.), Histochoice™ MB Fixative (Amresco, Solon, Ohio), RBC Fix™ (Isolab, Inc., Akron, Ohio), and Zinc Formal-Fixx™ (Shandon, Pittsburgh, Pa.). Other fixation methods such as microwaving are also amenable to FISH applications. Some sample types do not require fixative treatment for good hybridization. Others require fixative treatment to preserve the nuclear morphology and to yield good hybridization signal. The step at which a sample should be fixed needs to be determined empirically. After deposition onto filters, fixed or unfixed cells can still be responsive to reagents including NaOH, papain, and trypsin, and exhibit a change in nuclear morphology such as size. This may affect the hybridization results.

The DNA probes utilized were either single copy probes (100– 140 kb) consisting of cosmid contigs or were repetitive probes. The targets were nuclear DNA. For the 13, 18 and 21 cosmid contigs used, we expect 2 signals for normal cells and 3-4 signals for aneuploid cells.

In one preferred embodiment of the present invention, a 0.1 or 0.2 μm Costar (Cambridge, Mass.) polycarbonate membrane is placed over a 5 μm CellMicroSieves™ filter on a filter holder. The filter holder, a scintered glass type, is positioned on top of a vacuum flask. Tubing connects the vacuum flask to a vacuum source via a vacuum regulator set at 400 mm Hg. A cell suspension is pipetted onto the polycarbonate membrane. Once the fluid has passed through the membrane, the membrane filter is removed with forceps and air-dried. The membrane can either be stored at –20° C. until hybridization or it can be hybridized on the same day. For hybridization, 10 μl of wetting solution is pipetted onto a glass slide. The membrane filter is carefully placed on this drop in a fashion so as to minimize the formation of bubbles. Ten μl of hybridization cocktail is then placed on the membrane filter. A coverslip is then gently placed on the filter so as to minimize bubbles. The slide is then denatured at 80° C. for 9–13 min and incubated at 37° C. overnight in a humid chamber. The hybridization washes and analysis are as described in Example 1. Where there are a large number of samples, multiple membrane filters containing samples can be simultaneously hybridized and subsequently incubated with detection fluores in plastic bags. During hybridization and detection washes, filters can be washed freely or in mesh bags.

In another preferred embodiment, the 0.1 or 0.2 μm black polycarbonate membrane filter can be used to collect samples sorted with a FACS. The differences from the previous description are that instead of a vacuum flask, the filter holder is placed on top of a plexiglass structure to which the vacuum hose is attached. The entire device (membrane filter, CellMicroSieves™, filter holder, plexiglass structure) is situated so that the cell stream emanating from a FACS can be deposited directly or falls directly onto the membrane filter either in the presence of a constant vacuum or withholding the vacuum until the sort is complete. The membrane filter can be either dry or wet. If it is wet, the vacuum is withheld until the end of the sort. The vacuum can be withheld until the end of the sort only if the liquid collecting on the membrane is not overly excessive. The advantages of sorting cells directly onto a membrane filter instead of into a tube and then filtering the cells onto a membrane filter are that there is less cell loss, less sample handling and faster, easier sample processing. The rate at which rare cells are sorted onto the membrane filter can affect the quality of the resulting FISH. In the case of direct sorting onto dry membranes in the presence of a constant vacuum, fetal liver cells sorted quickly (approximately 20 sec or less) onto the membrane yielded better results than the same cells deposited over a period of several minutes. In experiments with fetal liver cells sorted for CD71, glycophorin A, and Hoechst 33342, good quality hybridization has been obtained with unfixed cells. When blood from pregnant women was sorted using the same parameters, it was found that best results were obtained with fixed cells. Fixing cells before sorting and after deposition onto membranes gave the best FISH results. For unsorted maternal samples, no fix was necessary for good hybridization results.

Following completion of FISH on membrane filters, analysis can take place either by a trained microscopist or by automated image processing. It is our goal to develop a FISH on membrane filters protocol that is totally compatible with automated image processing. This will necessitate making our samples as flat as possible. A three-dimensional target cell will render autofocusing a very difficult if not impossible task, and certainly complicates analysis even for a trained individual. A preferred embodiment would be to have the cells and signals in a single focal plane. This also simplifies analysis if samples are manually read.

The method of the present invention consists of depositing a cell or cell suspension onto a polymeric membrane filter by vacuum filtration. No reagent treatment is needed to permeabilize the cells further. DNA probes to single copy sequences as well as to repetitive sequences have been used successfully to probe for nuclear DNA on interphase and metaphase chromosomes. Our method results in nuclei that are sufficiently flat for rapid microscopic enumeration of chromosomes. The entire protocol is simpler than that standardly employed in laboratories, and is amenable to rapid processing of a large number of clinical samples.

EXAMPLE 1

Detection of DNA in Fetal Liver Cells Captured on Membrane Filters

Human fetal liver cells were fractionated on a Ficoll-Paque gradient (Pharmacia, Uppsala, Sweden). Cells were diluted with 2 volumes of Hank's Balanced Salt Solution (HBSS) or PBS in a 50 ml conical tube. Ten ml of diluted blood was pipetted into a 15 ml conical tube and Ficoll-Paque in a 9 inch Pasteur pipette was then placed beneath the blood sample. Tubes were spun in a tabletop centrifuge at 2000 RPM for 20 minutes at 25° C. The top layer containing the serum was removed and discarded. The mononuclear cell layer was removed to a fresh tube, rinsed twice in PBS, resuspended in complete RPMI 1640 (RPMI 1640, 10% fetal calf serum (FCS), 1% penicillin, 1% streptamycin) and counted in a hemocytometer.

Nucleated cell concentration was determined by spotting an aliquot onto either a 0.22 μm PVDF membrane filter (Millipore, Bedford, Mass.), or 0.1 or 0.2 μm polycarbonate membrane filter (Poretics, Livermore, Calif. or Costar, Cambridge, Mass.) and stained with a solution of DAPI antifade (500 μg/ml 4,6-diamidino-2-phenylindole (DAPI- Sigma, St. Louis, Mo.), 2.33% DABCO (Sigma, St. Louis Mo.), 20 mM Tris-HCl, pH 8.0, 90% v/v glyerol) to determine the number of nucleated cells. The number of DAPI-positive nuclei were then counted microscopically.

Cells were diluted in PBS to obtain a concentration of 100–400 cells/μl and a minimum of 5–10 μl of cells were then vacuum filtered onto the membrane filters as follows. The membrane filters were placed onto a dry 5 μm CellMicroSieves™ filter (Biodesign, Inc., Carmel, N.Y.) which was placed onto a scintered glass filtration apparatus (Kontes, Vineland, N.J.) and vacuum filtered at 400 mm Hg. Once the liquid had filtered through the membrane filters, the membrane was removed and air dried. Membrane filters were stored at −20° C.

The membrane filters were removed from storage and placed, cell side up, onto 10 µl of wetting solution (50% formamide, 6X SSC (1XSSC=0.15M NaCl, 0.15M Na Citrate pH 7.0), 10% (w/v) dextran sulfate) on a glass slide. Ten µl of hybridization cocktail (50% formamide, 6X SSC, 10% dextran sulfate, 200 ng/µl human Cot 1 DNA (GIBCO BRL, Life Technologies, Gathersburg, Md.), and 800 ng/µl salmon sperm DNA which was sonicated for 600 bp fragments) was placed on the membrane filters. A glass slide, parafilm or coverslip was placed over membrane filter. A DNA probe was included in the hybridization cocktail at the following concentrations: 10 ng/µl autosome probe, 0.5- 2.5 ng/µl X probe or 5 ng/µl Y probe. These probes and the protocol by which the probes were labeled are described in Klinger, K., et al., *Am. J. Hum. Genet.*, (1992) 51: 55.

The nucleic acids were denatured by incubating on a 80° C. slide warmer for 9–13 minutes. The membrane filters were then incubated overnight at 37° C. in a humid chamber.

After the incubation, the membrane filters were removed from the slides, and rinsed twice in 2X SSC, pH 7.0, to remove excess hybridization cocktail. The membrane filters were then washed in a batch process. The first 3 washes were for 5 minutes each at 42° C. in 50% formamide, 2XSSC, pH 7.0. The membrane filters were rinsed twice in 2XSSC, washed 3 times for 5 minutes each in 0.1 XSSC at 60° C., blocked in 3% BSA, 4xSSC at 42° C. for 5 minutes . They were then mounted on slides and incubated for 30 minutes at 37° C. in 4XSSC, 1% bovine serum albumin (BSA), 0.1% Tween 20 with appropriate detection fluors: streptavidin-Cy3™ (2.0 µg/ml; Jackson ImmunoResearch Laboratories, Inc. West Grove, Pa.), anti-digoxigenin-FITC (1.0 µg/ml; Boehringer Mannhelm, Indianapolis, Ind.), CyRO™ (250 ng/ml; Biological Detection Systems, Pittsburgh, Pa.) or avidin-FITC (5.0 µg/ml; Vector Laboratories, Burlingame, Calif.), and then covered with parafilm or a cover slip.

Membrane filters were then removed from slides and washed 3 times with 4XSSC 0.1% Tween 20 for 5 minutes at 42° C., rinsed in 2X SSC at room temperature, and placed on glass slides on which DAPI antifade had been placed. Approximately 25 µl DAPI antifade was placed on the membrane filters which were covered with a cover slip and sealed with nail polish.

Analysis was done using a Zeiss Axioplan or Axioscope epifluorescence microscope equipped with appropriate excitation and emission filters.

In genetically normal fetal liver cells, 2 signals for chromosome 13, 18 or 21 were detected per cell. In female fetal liver cells, two X signals were detected and in male fetal liver cells a single X signal and a single Y signal were detected.

EXAMPLE 2

Hybridization of Sorted Fetal Liver Cells Applied to Membrane Filters

Female fetal liver mononuclear cells were obtained as described in Example 1 and prepared for fluorescence activated cell sorting (FACS). Cells were resuspended in 1 ml PBS supplemented with 1% BSA following fractionation on a Ficoll Hypaque gradient. From this 1 ml sample, a 50 µl aliquot was removed for staining with an antibody to keyhole limpet hemocyanin (Becton Dickinson, San Jose, Calif.) and 20 µl aliquots were removed and stained with each antibody to be used. These aliquots were used to determine blackground autofluorescence of the cells. The remainder of the sample was stained with FITC-anti-CD71 (Becton Dickinson, San Jose, Calif.). For every 1 million cells in the sample, 10 µl of antibody was used for staining. Following the addition of antibody, the cells were vortexed and then incubated for 30 minutes on ice. They were spun down at setting 4 on the Eppendorf centrifuge model number 5415 (Eppendorf, Brinkmann Industries, Westbury, N.Y.). The solution was aspirated off and the cells were resuspended in 0.5–1 ml of PBS. Cells were then transferred to 6 ml polypropylene tubes for flow cytometry and FACS.

Sorted cells were vacuum filtered (400 mm Hg) onto 0.2 µm black polycarbonate (Costar) membrane filters. After hybridization with BioX (2.5 ng/µl) and simultaneously with Dig18 (10 ng/µl), the two X signals were easily visible while the 18 signal were of moderate to weak strength.

EXAMPLE 3

Detection of DNA in Cord Blood Using Labeled Nucleic Acid Probes on a PVDF Membrane Filter Mononuclear human cord blood cells were separated on a Ficoll gradient and approximately 500 cells were vacuum filtered onto 0.22 µm PVDF (Millipore) membrane filters. The filters were saturated with 75 mM KCl, incubated for 20 minutes at 37° C., and fixed for 10 minutes in 3:1 methanol:acetic acid. They were then dehydrated through an ethanol series (70%, 80%, 90%, 100%) for 30– 60 seconds each. Filters were hybridized with 40 µl of hybridization cocktail containing either the BioX (2.5 ng/µl), BioY (5 ng/µl), Bio 13 ( 10 ng/µl), Bio 18 ( 10 ng/µl) or Bio21 ( 10 ng/µl) probes. DNA was denatured for 10 minutes at 80° C., and the filters were hybridized overnight and washed as described in Example 1. There were good X and Y signals, and small sharp 13, 18 and 21 signals observed.

EXAMPLE 4

Detection of DNA in Fetal Liver Cells Using Labeled Nucleic Acid Probes on Various Membrane Filters Mononuclear fetal liver cells prepared as described in Example 1 were vacuum filtered (400 mm Hg) onto different types of filters: mixed esters of cellulose (Millipore and Whatman), nitrocellulose (Schleicher and Schuell), PVDF (Millipore), polyfluorotetraethylene (PFTE: Millipore), nylon (Schleicher and Schuell and Micron Separations Inc.), polysulfone (Gelman), and polycarbonate (Costar). They were hybridized with either BioXDigY or DigXBio21. Hybridization signal quality from best to worst was as follows: polycarbonate, PVDF, polysulfone, mixed esters of cellulose, nitrocellulose, PFTE, and nylon.

EXAMPLE 5

Detection of DNA in Maternal Sample Captured on a Polycarbonate Membrane Filter

A maternal blood sample, consisting of 20 ml blood obtained from a donor about to undergo amniocentesis and who, based on ultrasound, was believed to be carrying a male fetus, was treated as described in Example 1. Cells were stained by methods similar to those described in Example 2. The cells were stained with Hoechst 33342 for 30 minutes at 37° C., washed twice and then stained with monoclonal antibody conjugated to FITC. Cells were incubated at 4° C. for 45 minutes, washed twice and resuspended in 0.5 ml PBS. Cells were sorted into 0.5 ml PBS/2% FCS and vacuum filtered onto two 0.1 μm black Costar polycarbonate membranes which were hybridized with BioXDigY probes. Of the two filters, the first contained 414 nuclei, of which 315 were XX, 5 were XY, and 72 were unknown.

EXAMPLE 6

Fetal Liver Cells Sorted Directly onto PVDF and Polycarbonate Membranes

Mononuclear fetal liver cells were recovered from a Ficoll gradient and stained with a proprietary monoclonal antibody and with antibody against CD3. They were sorted for the target of the monoclonal antibody and for absence of CD3 directly onto 0.22 μm PVDF (Millipore) and 0.2 μm polycarbonate (Poretics) membrane filters. The filters were placed on a filter support derived from a disposable filter unit that had been dismantled. This filter support was placed onto an opening on a plexiglass device that also had an opening on the bottom to which a piece of tubing was connected. This tubing was attached to a house vacuum. This set up enabled us to vacuum filter the cells onto the membrane as they emerged from the sorter.

The membrane filters containing the cells were then processed in a variety of ways using various combinations of 100% ethanol, Optistain, 3:1 methanol:acetic acid or 75 mM KCl. Following processing, the membranes were then hybridized with BioXDig21 (X at 2.5 ng/μl and 21 at 10 ng/μl) and detected with Cy3™ as described in Example 1.

For both membrane types, there was no significant FITC background (i.e., autofluourescence that interfered with the target signal). The best processing protocol for the 0.2 μm polycarbonate membrane was to sort onto a dry membrane, air dry, immerse for 1 minute in Hematic Optistain II-A buffer (Gam Rad, San Juan Capistrano, Calif.), dry and hybridize. The best protocol for the 0.22 μm PVDF was the same as for the polycarbonate or to sort onto a dry membrane, immerse in 100% ethanol for 1 minute, Optistain for 1 minute, dry and hybridize. Best membranes had good strong Cy3™ and FITC signals, good nuclear morphology and were comparable to a good slide. Male fetal liver cells had 1 X signal, female fetal liver cells had 2 X signals and cells from either gender had two 21 signals.

EXAMPLE 7

Maternal Blood Cells Sorted Directly onto Polycarbonate Membrane Filters

Mononuclear cells (Ficolled separately and then pooled) from 3 pregnant women were stained with CD71, Glycophorin A and Hoechst 33342. A CellMicroSieves™ support filter was placed on the filter holder underneath the polycarbonate membrane. The cells were then sorted directly onto various dry polycarbonate membrane filters under constant (500 mm Hg) vacuum. Approximately 1,000 FACS events were sorted onto each membrane. The membranes were then hybridized with DigXBio13 and were then analyzed to determine which membranes exhibited the best signals.

TABLE 1

| Polycarbonate Membrane Filters | | |
|---|---|---|
| Pore Size (μm) | Color | Manufacturer |
| 0.1 | Black | Costar |
| 0.2 | Black | Costar |
| 0.6 | Black | Costar |
| 0.8 | Black | Costar |
| 5.0 | Black | Costar |
| 0.22 | Black | Micron Separations Inc. |
| 0.45 | Black | Micron Separations Inc. |
| 0.2 | Black | Millipore |
| 0.4 | Black | Millipore |
| 0.1 | White | Poretics |
| 0.2 | White | Poretics |
| 0.4 | Black | Poretics |

Autofluorescence made it difficult to read hybridization signals membranes manufactured by Micron Separations Inc. and Millipore. Membranes with pore sizes greater than 0.22 μm retained nuclei drawn into the filter pores, rendering the nuclei very three dimensional and complicating the analysis. The 0.1, 0.2, 0.6 and 0.8 m membranes manufactured by Costar and the 0.1 and 0.2 μm Poretics membranes gave the best hybridization signals. Hybridization signals were clean and strong.

EXAMPLE 8

Preparation of Maternal Samples Sorted Directly onto Polycarbonate Membranes for FISH Peripheral blood (20 ml) from 3 pregnant women were separated on Ficoll-Paque separately and the mononuclear cell layer was removed (see Example 1) and pooled. Cells were then stained for CD71, glycophorin A, Hoechst No. 33352 (as in Example 2) and aliquots were treated with various fixatives for the times shown in Table 2. Following treatment with each presort fixative, cells were pelleted for 4 minutes at setting 4 in an Eppendorf centrifuge and rinsed twice in PBS. The rinsed pellet was resuspended in PBS and sorted onto black dry 0.1 μm polycarbonate membranes (Costar) as described in Example 6. Once the cell suspension was completely filtered onto the membrane, it was removed from the filtration apparatus and fixed postsort as shown in Table 2. Cells from each presort fix condition were direct sorted onto 10 membrane filters, each of which was then treated with 1 of the postsort fix treatments. The membrane filters were air dried and stored at −20° C. until hybridization.

TABLE 2

| Fixatives | | |
|---|---|---|
| Fixative Step | Presort Fixative | Fixation Time (Min) |
| Presort | No fix | 0 |
| Presort | 0.5% formaldehyde in PBS | 2 |
| Presort | 0.5% formaldehyde in PBS | 12 |
| Presort | 1% para formaldehyde in PBS | 2 |
| Presort | 1% para formaldehyde in PBS | 12 |
| Presort | Streck's Tissue Fixative (S.T.F. ™) | 2 |
| Presort | S.T.F. ™ | 25 |
| Postsort | No fix | 0 |
| Postsort | 0.5% formaldehyde in PBS | 2 |
| Postsort | 0.5% formaldehyde in PBS | 12 |
| Postsort | 0.5% formaldehyde in PBS | 15 |
| Postsort | 1% paraformaldehyde in PBS | 2 |
| Postsort | 1% paraformaldehyde in PBS | 15 |

TABLE 2-continued

Fixatives

| Fixative Step | Presort Fixative | Fixation Time (Min) |
|---|---|---|
| Postsort | S.T.F. ™ | 2 |
| Postsort | S.T.F. ™ | 15 |
| Postsort | S.T.F. ™ | 30 |
| Postsort | S.T.F. ™ | 60 |

Membranes were hybridized BioXDig21, and washed as described in Example 1. Samples were analyzed and the best from each presort fix group were then ranked on the strength and discreteness of the chromosome 21 signal and on nuclear morphology.

The best presort conditions were either no fix or 25 minutes S.T.F.™. The best postsort fixatives were 2, 15 and 30 minutes S.T.F.™. In general, the 2 and 12 minutes formaldehyde presort fixatives resulted in little or no signal. The worst postsort fixatives used in combination with a presort fix were: 2 and 12 minutes formaldehyde, 60 minutes S.T.F.™ and 15 minutes formaldehyde. The best conditions contained cells with 2 strong, discrete chromosome 21 signals and 2 strong X signals. The best conditions overall were: presort fixed with S.T.F.™ for 25 minutes and postsort fixed with S.T.F.™ for 2 minutes. Hybridization efficiency for the chromosome 21 probe was 100%. The second best condition was unfixed presort and fixed with S.T.F.™ for 2 minutes postsort; compared to the best condition, the nuclear morphology in this sample was poorer and the hybridization efficiency was lower (96%) than with the best condition. The next best conditions were 2 minutes paraformaldehyde presort fix plus 2 minutes S.T.F.™ postsort fix and 12 minutes paraformaldehyde presort fix with 2 minutes S.T.F.™ postsort fix.

EXAMPLE 9

Detection of DNA in Human Fetal Liver Cells and Adult PBMCs Sorted Directly onto Polycarbonate Membrane Filters Human male fetal liver cells were prepared as described in Example 1. Blood from 2 pregnant women was Ficolled separately and then pooled. Both the pooled maternal sample and the fetal liver sample were then separately stained with CD71, glycophorin A and Hoechst 33342 as described in Example 2. The cells were counted, and some of the fetal liver cells were then spiked into the maternal cells at a ratio of 1 fetal liver cell: 250 maternal cells. The fetal/maternal cell mixture as well as the pure maternal cell population were sorted using the Becton Dickinson Vantage FACS onto black 0.1 µm Costar polycarbonate membranes placed on the apparatus described in Example 7. A total of 1,500 FACS events were sorted onto each membrane. The vacuum pressure was set at 350 mm Hg. The membranes were hybridized with DigXBio18 according to the procedure detailed in Example 1.

The cells were sorted onto a polycarbonate membrane that was either dry (as in Examples 6–8) or wetted in various solutions (PBS, 2X PBS, 10% glycerol in PBS, 35 mM KCl, or nuclear isolation buffer (NIB; 250 mM sucrose, 25 mM NaCl, 10 mM PIPES, 1.5 mM $MgCl_2$, 5 mM spermidine, pH 7.0 with HCl). For the wet membranes, the vacuum was not turned on until the sort was completed. For the dry membranes, one set was made with a continuous vacuum throughout the sort and the other set was made with no vacuum until the sort was completed. The final variable tested was the presence or absence of a 5 µm CellMicroSieves™ membrane as a support. In those situations where the polycarbonate membranes were wet, the support membrane was also wetted with the same solution. A dry CellMicroSieves™ membrane was used when a dry polycarbonate membrane was placed onto the apparatus.

Membrane filters were analyzed for signal quality, nuclear background and nuclear morphology. For each wet/dry/vacuum condition, a determination was first made as to whether the presence or absence of a CellMicroSieves™ membrane was preferred. The seven membranes with the preferred CellMicroSieves™ configuration were then rated relative to each other. The spiked samples were analyzed by one individual and the maternal samples were analyzed by another individual. For the fetal liver/maternal spike, there was no consistent difference in signal or nuclear background observed in the 2 cell types. The lobular or irregular nuclei were usually maternal and the fetal nuclei tended to be round. In general, when CellMicroSieves™ support was present, the DAPI-stained nuclei were larger and less bright, and there tended to be fewer irregularly shaped nuclei that stained unevenly with DAPI. The sample application preferences for the spikes and maternal sample are detailed in Tables 3A and 3B.

TABLE 3A

Preferred Sample Applications for Spiked Samples

| Rank | Wet or Dry/Vacuum | MicroSieves |
|---|---|---|
| 1 | Wet with 1:1 KCl/End | Yes |
| 2 | Dry/Constant | No |
| 3 | Dry/End | No |
| 3 | Wet with 10% glycerol/End | Yes |
| 3 | Wet with PBS/End | Yes |
| 4 | Wet with 2X PBS/End | No |
| 5 | Wet with NIB/End | Yes |

TABLE 3B

Preferred Sample Applications for Maternal Samples.

| Rank | Wet/Dry/Vacuum | MicroSieves |
|---|---|---|
| 1 | Wet with PBS/End | No |
| 2 | Wet with 1:1 KCl/End | Yes |
| 3 | Dry/Constant | Yes |
| 4 | Wet with 2X PBS/End | No |
| 5 | Wet with 10% glycerol/End | Yes |
| 6 | Wet with NIB/End | Yes |
| 7 | Dry/End | No |

Prewetting the filters affected the nuclear distribution. Nuclear background was affected by some of the solutions, such as the KCl and 2X PBS. Although a variety of cells were seen on most filters, there were some that yielded worse nuclei overall than others, e.g., NIB. When the hybridizations were optimal, there were 2 chromosome 18 signals for both the maternal and fetal cells. The male fetal cells contained 1 X chromosome signal and the adult female cells contained 2 X signals.

EXAMPLE 10

Hybridization of Human Adult Lymphocytes Vacuum Filtered Onto Polycarbonate Membrane Filters Mononuclear adult blood cells were recovered from a Ficoll gradient. Following determination of the nucleated cell concentration, the suspension was diluted to 200 cells/μl and 5 μl was vacuum filtered onto 0.2 μm polycarbonate (Costar) membranes at 400 mm Hg. As described in Example 1, the membranes were then hybridized with XY probes (0.5 ng/μl X and 5 ng/μl Y) and washed. Fluorescence microscopy showed that the male adult cells contained an X and Y signal and the female adult cells contained two X signals.

EXAMPLE 11

Hybridization of Human Erythroleukemic (HEL) Cells Vacuum Filtered onto Polycarbonate Membrane Filters HEL cells were washed and resuspended in PBS. Cells were then vacuum filtered onto 0.2 μm black Costar polycarbonate membranes. The membranes were hybridized with BioXDigY and DigXBio21 as described in Example 1. The nuclei showed one X, two Y and four 21 signals or alternatively one X, one Y and four 21 signals.

EXAMPLE 12

Hybridization to DNA of Amniocytes on a Polycarbonate Membrane

Samples of pooled amniotic fluid and fetal liver cells were settled according to a method described in Klinger, K. W., et al., *Am. J. Hum. Genet.*, (1992)51: 55, with the modification of using wet (PBS) 0.1 μm pore black Costar membranes placed onto glass slides. The samples were also vacuum filtered onto the membranes using the methods described in Example 1. The hybridization of amniocytes and fetal liver cells on membranes was compared to that obtained with the same cells settled onto slides. Membranes and slides were hybridized with BioXDigY and washed according to the specifications in Example 1. Signal strength and quality for amniocytes settled onto membranes was comparable to that observed with amniocytes settled onto glass slides. Fetal liver cells gave slightly better signal when settled onto slides than when settled onto wet or dry membranes. Signal strength and quality for amniocytes and fetal liver cells filtered onto membranes were much better than those on cells settled onto slides or filters.

EXAMPLE 13

Simultaneous, Efficient Processing of Multiple Samples on Membrane Filters

Fetal liver samples were spotted in each quadrant of eleven 0.2 μm black Costar membrane filters. The membrane filters were then cut into 2 halves, each receiving two fetal liver sample sites. Each set of ten semicircular membrane filters was then stacked on top of each other and placed in a plastic bag. A total of 50 μl of hybridization cocktail containing Bio 13 (10 ng/μl) and DigX probe (1.5 ng/μl) was added to one bag prior to sealing. The second bag received 25 μl Of the same cocktail as well as 25 μl of wetting solution prior to sealing. DNA and probes on stacked membranes were denatured by placing bags in an 80° C. water bath for 10 minutes. The bags were then incubated at 37° C. overnight. The eleventh membrane filter was split in half and both parts were hybridized according to our standard procedure detailed in Example 1. Both were placed on slides; one membrane was hybridized with 10 μl Of cocktail and the second was hybridized with 5 μl cocktail diluted with 5 μl of wetting solution. The membrane filters were then all washed by our standard protocol. Hybridization signal was detected by performing the detection step with all the membranes in a bag before being mounted individually on slides. The results were that the membrane filters in the center of each stack contained nuclei with X and 13 signals that were indistinguishable in strength and quality from membrane filters at the ends of the stack or from the membrane filter that was hybridized on a slide. In addition, the membrane filters with the more concentrated hybridization cocktail (i.e., without the wetting solution) gave a stronger hybridization signal.

EXAMPLE 4

Preparation of Multiple Samples on Dot Blot Apparatus Followed by FISH

A rectangular piece of black 0.2 μm Costar polycarbonate membrane filter was sandwiched into dot blot apparatus (96 Well Convertible Filtration Manifold System - GIBCO BRL). Twenty five μl of fetal cells resuspended in PBS was pipetted into each well, and vacuum (400 mm Hg) was applied to filter the cells onto the membrane. A CellMicroSieves™ 5 μm support filter was used under some of the polycarbonate membranes. Three different fetal liver samples were applied 24 times to each filter, such that the membrane containing 96 samples could be cut up into 24 sections, each section having 3 different fetal liver samples. Each section also had a site that was used for numbering membranes. After the membrane was cut up into 24 sections, hybridization with DigX (2.5 ng/μl) and BioY (5 ng/μl) using the standard protocol outlined in Example 1 showed strong discrete X and Y signals for the male cells and two strong and discrete X signals for female samples. There was a slight preference for preparations made with the CellMicroSieves™ support. These results were comparable to hybridization results that we routinely obtain with filters made on the glass scintered filter holders.

EXAMPLE 15

NaOH Treatment Affects Nuclear Size and Hybridization Signals

Fetal liver mononuclear cells were diluted into PBS (20 cells/μl) and 500 cells were vacuum filtered onto 0.2 μm white polycarbonate (Poretics),and 0.22 μm PVDF (Millipore) membranes. The membranes were then air dried prior to further processing through 1 of 3 protocols. Protocol 1 consisted of immmersing membranes sequentially for 2 minutes in 0.5M NaOH, neutralization buffer (1.5M NaCl. 0.5M Tris-HCl, pH 8.0), 2X SSC, and Optistain, then dried 5 minutes at 65° C. Protocol 2 membranes were immersed sequentially for 2 minutes in Optistain, 0.5M NaOH, and neutralization buffer, then dried for 5 minutes at 65° C. Membranes for protocol 3 were immersed for 3 minutes in 0.5M NaOH, 2 minutes in neutralization buffer, 2 minutes in Optistain and then dried for 5 minutes at 65° C. The Optistain control membranes were immersed in Optistain and then dried. Membrane filters were then hybridized with BioXDig21. For the PVDF membranes, 30 µl of wetting solution and 30 µl hybridization cocktail was used, while the polycarbonate required 10 µl of wetting solution and 10 µl of hybridization cocktail. Denaturation was for 13 minutes at 80° C. Membranes were hybridized and washed as described in Example 1. The fluors used were anti-dig-FITC and avidin CyRO™.

TABLE 4

The Effects of NaOH

| Pro-tocol | Polycarbonate | PVDF |
|---|---|---|
| Opti-stain Con-trol | Brightest DAPI, smoothest nuclear edges. Hybridization signals for X and 21 visible. | Autofluorescence, uneven nuclear edges. X signal visible, but 21 visible only in few nuclei. |
| 1 | Large (3X diameter) nuclei with smooth edges, grainy DAPI. Fragmented X and 21 signals. | Size and nuclear edges unchanged from Optistain control. Grainy DAPI, autofluorescent. X and 21 signals slightly stronger than on controls. Signals also fragmented. |
| 2 | Size similar to Optistain sample. DAPI similar to Protocol 1. Some regions have normal sized nuclei with good signal (better than Optistain control). Other regions have larger, unevenly-stained DAPI nuclei with fragmented signal. | Pale, uneven DAPI. Size similar to Optistain. Autofluorescent. Dim, fragmented X signal. Chromosome 21 signal is not detectable in most nuclei and barely detectable in a few. |
| 3 | Large (3X) nuclei, with uneven DAPI. Bright fragmented signals. | Size same as above. Uneven, grainy DAPI. Bright, slightly fragmented X signals. Chromosome 21 signals weakly visible. |

These results show that each membrane filter has different optimal conditions for hybridization. In addition, they show that unfixed cells on membrane filters can still respond to reagents by a change in nuclear size.

EXAMPLE 16

Comparison of Cell Retention of Cord Blood Cells Either Filtered onto PVDF Membrane Filters or Cytospun onto Glass Slides Mononuclear cells from two cord bloods were each recovered from a Ficoll gradient, resuspended in RPMI 1640 medium containing fetal calf serum and then quantitated. Approximately 300 cells from cord blood sample #1 and 150 cells from cord blood #2 were filtered onto PVDF filters under 650 mm Hg of vacuum pressure and air dried. The same number of cells from each cord blood sample were cytospun (Cytospin 3, Shandon Lipshaw, Pittsburgh, Pa.) onto a glass microscope slides under the following conditions: 800 rpm, 5 minutes, low acceleration. The PVDF filters and glass microscope slides were stained with DAPI antifade and scored. For cord blood #1, the mean cell retention on PVDF filters was 353 cells (118%) as compared to the cell retention on the cytospun glass slides which was 165 cells (55%). Cord blood #2 showed similiar results with the mean number of cell retained on PVDF filters being 147 (98%) as compared to the cell retention on the cytospun glass slides which was 103 (69%). Retention of cord blood cells was better when the cells were filtered onto PVDF membrane filters than when cytospun onto glass slides.

EQUIVALENTS

Those skilled in the art will recognize, or be able to ascertain, using no more than routine experimentation many equivalents to the specific embodiments of the invention described herein. Such equivalents are intended to be encompassed by the following claims:

We claim:

1. A method for detecting a target DNA in a morphologically identifiable cell in situ, comprising:
   a. depositing a cell onto a polymeric membrane filter wherein the cell is retained on the polymeric membrane filter and the DNA is available for in situ hybridization with a labeled nucleic acid probe specific for the target DNA;
   b. incubating the polymeric membrane filter with a non-isotopically labeled nucleic acid probe for a period of time sufficient for hybridization of the nucleic acid probe to the target DNA; and
   c. detecting the nucleic acid probe in situ wherein detection of the nucleic acid probe is indicative of the presence of the target DNA.

2. The method of claim 1, wherein the cell is mammalian.

3. The method of claim 1, wherein the polymeric membrane filter is made of polycarbonate.

4. The method of claim 1, wherein the polymeric membrane filter is made of polyvinylidene fluoride.

5. The method of claim 1, wherein the cell is treated with a fixative prior to step a).

6. The method of claim 1, wherein the polymeric membrane filter is treated with a fixative after step a).

7. A method for detecting a target DNA in a morphologically identifiable cell in situ, comprising:
   a. filtering a cell onto a polymeric membrane filter, wherein the cell is retained on the filter and the DNA is available for in situ hybridization with a labeled nucleic acid probe specific for the target DNA;
   b. incubating the polymeric membrane filter with a non-isotopically labeled nucleic acid probe for a period of time sufficient for hybridization of the nucleic acid probe to the target DNA; and detecting the nucleic acid probe in situ wherein detection of the nucleic acid probe is indicative of the presence of the target DNA.

8. The method of claim 7, wherein the cell is mammalian.

9. The method of claim 7, wherein the polymeric membrane filter is made of polycarbonate.

10. The method of claim 7, wherein the polymeric membrane filter is made of polyvinylidene fluoride.

11. The method of claim 7, wherein the cell is treated with a fixative prior to step a).

12. The method of claim 7, wherein the polymeric membrane filter is treated with a fixative after to step a).

13. A method for detecting a target DNA in a nucleus in situ, comprising:
   a. depositing a morphologically identifiable cell onto a polymeric membrane filter wherein the nucleus is retained on the polymeric membrane filter and the DNA is available for in situ hybridization with a labeled nucleic acid probe specific for the target DNA;
   b. incubating the polymeric membrane filter with a non-isotopically labeled nucleic acid probe for a period of time sufficient for hybridization of the nucleic acid probe to the target DNA; and c. detecting the nucleic acid probe in situ wherein detection of the nucleic acid probe is indicative of the presence of the target DNA.

14. The method of claim 13, wherein the nucleus is mammalian.

15. The method of claim 13, wherein the polymeric membrane filter is made of polycarbonate.

16. The method of claim 13, wherein the polymeric membrane filter is made of polyvinylidene fluoride.

17. The method of claim 13, wherein the cell is treated with a fixative prior to step a).

18. The method of claim 13, wherein the polymeric membrane filter is treated with a fixative after step a).

19. A method for detecting a target DNA in a nucleus in situ, comprising:
   a. filtering a morphologically identifiable cell onto a polymeric membrane filter, wherein the nucleus is retained and the DNA is available for in situ hybridization with a labeled nucleic acid probe specific for the target DNA;
   b. incubating the polymeric membrane filter with a non-isotopically labeled nucleic acid probe for a period of time sufficient for hybridization of the nucleic acid probe to the target DNA; and
   c. detecting the nucleic acid probe in situ wherein detection of the nucleic acid probe is indicative of the presence of the target DNA.

20. The method of claim 19, wherein the nucleus is mammalian.

21. The method of claim 19, wherein the polymeric membrane filter is made of polycarbonate.

22. The method of claim 19, wherein the polymeric membrane filter is made of polyvinylidene fluoride.

23. The method of claim 19, wherein the cell is treated with a fixative prior to step a).

24. The method of claim 19, wherein the polymeric membrane filter is treated with a fixative after to step a).

* * * * *